(12) United States Patent
Markowitz et al.

(10) Patent No.: US 8,135,467 B2
(45) Date of Patent: Mar. 13, 2012

(54) CHRONICALLY-IMPLANTABLE ACTIVE FIXATION MEDICAL ELECTRICAL LEADS AND RELATED METHODS FOR NON-FLUOROSCOPIC IMPLANTATION

(75) Inventors: H. Toby Markowitz, Roseville, MN (US); Chad Giese, St. Paul, MN (US); Steven L. Waldhauser, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 221 days.

(21) Appl. No.: 12/492,906

(22) Filed: Jun. 26, 2009

(65) Prior Publication Data

US 2010/0004724 A1 Jan. 7, 2010

Related U.S. Application Data

(63) Continuation of application No. PCT/US2007/089087, filed on Dec. 28, 2007.

(60) Provisional application No. 60/912,610, filed on Apr. 18, 2007.

(51) Int. Cl.
*A61N 1/00* (2006.01)
(52) U.S. Cl. .......................................... 607/27
(58) Field of Classification Search .................. 607/116, 607/27, 127, 129, 122, 120
See application file for complete search history.

(56) References Cited

U.S. PATENT DOCUMENTS

| | | | |
|---|---|---|---|
| 3,837,347 A | 9/1974 | Tower | |
| 3,995,623 A | 12/1976 | Blake et al. | |
| 4,506,680 A | 3/1985 | Stokes | |
| 4,619,246 A | 10/1986 | Molgaard-Nielsen et al. | |
| 4,696,304 A | 9/1987 | Chin | |
| 4,801,297 A | 1/1989 | Mueller | |
| 5,035,246 A | 7/1991 | Heuvelmans et al. | |
| 5,076,285 A | 12/1991 | Hess et al. | |
| 5,078,714 A | 1/1992 | Katims | |
| 5,099,845 A | 3/1992 | Besz et al. | |
| 5,167,239 A | 12/1992 | Cohen et al. | |
| 5,255,680 A | 10/1993 | Darrow et al. | |
| 5,265,622 A | 11/1993 | Barbere | |
| 5,342,295 A | 8/1994 | Imran | |

(Continued)

FOREIGN PATENT DOCUMENTS

EP 363117 4/1990

(Continued)

OTHER PUBLICATIONS

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

(Continued)

*Primary Examiner* — George Manuel
*Assistant Examiner* — Robert Wieland

(57) ABSTRACT

Bio-impedance may be used for navigation systems to chronically implant pacing and defibrillation leads in the heart using a non-fluoroscopic position sensing unit (PSU). Such a system requires that a conductive material, such as a retractable helical tip-electrode, be exposed during implantation. Since the tip is retracted during implantation, this disclosure provides a modified distal portion employing at least one aperture (or "window") for fluid exposure of the helix-electrode and a deployable internal sleeve for covering the aperture(s) when the helix-electrode is extended.

12 Claims, 7 Drawing Sheets

U.S. PATENT DOCUMENTS

| | | | |
|---|---|---|---|
| 5,385,148 | A | 1/1995 | Lesh et al. |
| 5,391,199 | A | 2/1995 | Ben-Haim |
| 5,443,489 | A | 8/1995 | Ben-Haim |
| 5,480,422 | A | 1/1996 | Ben-Haim |
| 5,512,920 | A | 4/1996 | Gibson |
| 5,522,874 | A | 6/1996 | Gates |
| 5,546,951 | A | 8/1996 | Ben-Haim |
| 5,558,091 | A | 9/1996 | Acker et al. |
| 5,568,809 | A | 10/1996 | Ben-haim |
| 5,639,276 | A | 6/1997 | Weinstock et al. |
| 5,697,377 | A | 12/1997 | Wittkampf |
| 5,713,946 | A | 2/1998 | Ben-Haim |
| 5,797,849 | A | 8/1998 | Vesely et al. |
| 5,800,407 | A | 9/1998 | Eldor et al. |
| 5,840,025 | A | 11/1998 | Ben-Haim |
| 5,916,193 | A | 6/1999 | Stevens et al. |
| 5,944,022 | A | 8/1999 | Nardella et al. |
| 5,983,126 | A | 11/1999 | Wittkampf |
| 6,009,349 | A | 12/1999 | Mouchawar et al. |
| 6,088,527 | A | 7/2000 | Rybczynski |
| 6,122,552 | A | 9/2000 | Tockman et al. |
| 6,152,946 | A | 11/2000 | Broome et al. |
| 6,196,230 | B1 | 3/2001 | Hall et al. |
| 6,236,886 | B1 | 5/2001 | Cherepenin et al. |
| 6,246,468 | B1 | 6/2001 | Dimsdale |
| 6,256,121 | B1 | 7/2001 | Lizotte et al. |
| 6,301,498 | B1 | 10/2001 | Greenberg et al. |
| 6,330,356 | B1 | 12/2001 | Sundareswaran et al. |
| 6,389,187 | B1 | 5/2002 | Greenaway et al. |
| 6,470,205 | B2 | 10/2002 | Bosselmann et al. |
| 6,546,270 | B1 | 4/2003 | Goldin et al. |
| 6,569,160 | B1 | 5/2003 | Goldin et al. |
| 6,574,498 | B1 | 6/2003 | Gilboa |
| 6,595,989 | B1 | 7/2003 | Schaer |
| 6,602,271 | B2 | 8/2003 | Adams et al. |
| 6,611,141 | B1 | 8/2003 | Schulz et al. |
| 6,701,176 | B1 | 3/2004 | Halperin et al. |
| 6,714,806 | B2 | 3/2004 | Iaizzo et al. |
| 6,868,195 | B2 | 3/2005 | Fujita et al. |
| 6,888,623 | B2 | 5/2005 | Clements |
| 6,892,091 | B1 | 5/2005 | Ben-Haim et al. |
| 6,990,370 | B1 | 1/2006 | Beatty et al. |
| 7,020,522 | B1 | 3/2006 | Hoijer et al. |
| 7,047,073 | B2 | 5/2006 | Hoijer et al. |
| 7,189,208 | B1 | 3/2007 | Beatty et al. |
| 7,207,989 | B2 | 4/2007 | Pike, Jr. et al. |
| 7,215,430 | B2 | 5/2007 | Kacyra et al. |
| 7,263,397 | B2 | 8/2007 | Hauck et al. |
| 7,305,121 | B2 | 12/2007 | Kaufmann et al. |
| 7,369,901 | B1 * | 5/2008 | Morgan et al. ................ 607/127 |
| 7,421,300 | B2 | 9/2008 | Smits et al. |
| 7,479,141 | B2 | 1/2009 | Kleen et al. |
| 2001/0031920 | A1 | 10/2001 | Kaufman et al. |
| 2002/0045810 | A1 | 4/2002 | Ben-Haim |
| 2002/0049375 | A1 | 4/2002 | Strommer et al. |
| 2002/0077544 | A1 | 6/2002 | Shahidi |
| 2002/0111662 | A1 | 8/2002 | Iaizzo et al. |
| 2002/0147488 | A1 | 10/2002 | Doan et al. |
| 2002/0183817 | A1 | 12/2002 | Van Venrooij et al. |
| 2003/0028118 | A1 | 2/2003 | Dupree et al. |
| 2003/0055324 | A1 | 3/2003 | Wasserman |
| 2003/0078494 | A1 | 4/2003 | Panescu et al. |
| 2003/0108853 | A1 | 6/2003 | Chosack et al. |
| 2003/0114908 | A1 | 6/2003 | Flach |
| 2003/0225434 | A1 | 12/2003 | Glantz et al. |
| 2003/0231789 | A1 | 12/2003 | Willis et al. |
| 2004/0001075 | A1 | 1/2004 | Balakrishnan et al. |
| 2004/0064159 | A1 | 4/2004 | Hoijer et al. |
| 2004/0068312 | A1 * | 4/2004 | Sigg et al. .................... 607/120 |
| 2004/0070582 | A1 | 4/2004 | Smith et al. |
| 2004/0097805 | A1 | 5/2004 | Verard et al. |
| 2004/0162599 | A1 | 8/2004 | Kurth |
| 2004/0215298 | A1 | 10/2004 | Richardson et al. |
| 2004/0228453 | A1 | 11/2004 | Dobbs et al. |
| 2004/0236395 | A1 | 11/2004 | Iaizzo et al. |
| 2004/0249281 | A1 | 12/2004 | Olstad |
| 2004/0249430 | A1 * | 12/2004 | Martinez et al. ............. 607/122 |
| 2004/0254437 | A1 | 12/2004 | Hauck et al. |
| 2005/0018888 | A1 | 1/2005 | Zonneveld |
| 2005/0119550 | A1 | 6/2005 | Serra et al. |
| 2005/0177151 | A1 | 8/2005 | Coen et al. |
| 2005/0187432 | A1 | 8/2005 | Hale et al. |
| 2005/0245803 | A1 | 11/2005 | Glenn Jr. et al. |
| 2006/0013523 | A1 | 1/2006 | Childers et al. |
| 2006/0058604 | A1 | 3/2006 | Avinash et al. |
| 2006/0117773 | A1 | 6/2006 | Street et al. |
| 2006/0153468 | A1 | 7/2006 | Solf et al. |
| 2006/0173268 | A1 | 8/2006 | Mullick et al. |
| 2006/0200049 | A1 | 9/2006 | Leo et al. |
| 2006/0206157 | A1 | 9/2006 | Hoijer |
| 2006/0229513 | A1 | 10/2006 | Wakai |
| 2006/0229594 | A1 | 10/2006 | Francischelli et al. |
| 2006/0247520 | A1 | 11/2006 | McGee |
| 2007/0016084 | A1 | 1/2007 | Denault |
| 2007/0038052 | A1 | 2/2007 | Swoyer et al. |
| 2007/0043413 | A1 | 2/2007 | Eversull et al. |
| 2007/0046661 | A1 | 3/2007 | Ma et al. |
| 2007/0049817 | A1 | 3/2007 | Preiss et al. |
| 2007/0112388 | A1 | 5/2007 | Salo |
| 2007/0123944 | A1 | 5/2007 | Zdeblick |
| 2007/0135721 | A1 | 6/2007 | Zdeblick |
| 2007/0135803 | A1 | 6/2007 | Belson |
| 2007/0156019 | A1 | 7/2007 | Larkin et al. |
| 2007/0164900 | A1 | 7/2007 | Schneider et al. |
| 2007/0167801 | A1 | 7/2007 | Webler et al. |
| 2007/0252074 | A1 | 11/2007 | Ng et al. |
| 2007/0270682 | A1 | 11/2007 | Huang et al. |
| 2007/0299351 | A1 | 12/2007 | Harlev et al. |
| 2007/0299352 | A1 | 12/2007 | Harlev et al. |
| 2007/0299353 | A1 | 12/2007 | Harlev et al. |
| 2008/0015466 | A1 | 1/2008 | Lerman |
| 2008/0024493 | A1 | 1/2008 | Bordoloi et al. |
| 2008/0038197 | A1 | 2/2008 | John et al. |
| 2008/0058656 | A1 | 3/2008 | Costello et al. |
| 2008/0071142 | A1 | 3/2008 | Gattani et al. |
| 2008/0118117 | A1 | 5/2008 | Gauldie et al. |
| 2008/0132800 | A1 | 6/2008 | Hettrick et al. |
| 2008/0183072 | A1 | 7/2008 | Robertson et al. |
| 2008/0207997 | A1 | 8/2008 | Higgins et al. |
| 2008/0243025 | A1 | 10/2008 | Holmstrom et al. |
| 2008/0249375 | A1 | 10/2008 | Obel |
| 2009/0017430 | A1 | 1/2009 | Muller-Daniels et al. |
| 2009/0063118 | A1 | 3/2009 | Dachille et al. |
| 2009/0093857 | A1 | 4/2009 | Markowitz et al. |
| 2009/0099619 | A1 | 4/2009 | Lessmeier et al. |
| 2009/0103793 | A1 | 4/2009 | Borland et al. |
| 2009/0126575 | A1 | 5/2009 | Son et al. |
| 2009/0129477 | A1 | 5/2009 | Yang |
| 2009/0131955 | A1 | 5/2009 | Wenderow et al. |
| 2009/0192381 | A1 | 7/2009 | Brockway et al. |
| 2009/0227861 | A1 | 9/2009 | Ganatra et al. |
| 2009/0253976 | A1 | 10/2009 | Harlev et al. |
| 2009/0262109 | A1 | 10/2009 | Markowitz et al. |
| 2009/0262979 | A1 | 10/2009 | Markowitz et al. |
| 2009/0262980 | A1 | 10/2009 | Markowitz et al. |
| 2009/0262982 | A1 | 10/2009 | Markowitz et al. |
| 2009/0262992 | A1 | 10/2009 | Markowitz et al. |
| 2009/0264727 | A1 | 10/2009 | Markowitz et al. |
| 2009/0264738 | A1 | 10/2009 | Markowitz et al. |
| 2009/0264739 | A1 | 10/2009 | Markowitz et al. |
| 2009/0264740 | A1 | 10/2009 | Markowitz et al. |
| 2009/0264741 | A1 | 10/2009 | Markowitz et al. |
| 2009/0264742 | A1 | 10/2009 | Markowitz et al. |
| 2009/0264743 | A1 | 10/2009 | Markowitz et al. |
| 2009/0264744 | A1 | 10/2009 | Markowitz et al. |
| 2009/0264745 | A1 | 10/2009 | Markowitz et al. |
| 2009/0264746 | A1 | 10/2009 | Markowitz et al. |
| 2009/0264747 | A1 | 10/2009 | Markowitz et al. |
| 2009/0264748 | A1 | 10/2009 | Markowitz et al. |
| 2009/0264749 | A1 | 10/2009 | Markowitz et al. |
| 2009/0264750 | A1 | 10/2009 | Markowitz et al. |
| 2009/0264751 | A1 | 10/2009 | Markowitz et al. |
| 2009/0264752 | A1 | 10/2009 | Markowitz et al. |
| 2009/0264777 | A1 | 10/2009 | Markowitz et al. |
| 2009/0264778 | A1 | 10/2009 | Markowitz et al. |
| 2009/0265128 | A1 | 10/2009 | Markowitz et al. |
| 2009/0267773 | A1 | 10/2009 | Markowitz et al. |

| | | | |
|---|---|---|---|
| 2009/0297001 | A1 | 12/2009 | Markowitz et al. |
| 2010/0030298 | A1 | 2/2010 | Martens et al. |
| 2010/0152571 | A1 | 6/2010 | Hartmann et al. |
| 2011/0054304 | A1 | 3/2011 | Markowitz et al. |

FOREIGN PATENT DOCUMENTS

| | | |
|---|---|---|
| EP | 1393674 A1 | 3/2004 |
| EP | 1421913 A1 | 5/2004 |
| EP | 2136706 | 12/2009 |
| WO | WO-9848722 A1 | 11/1998 |
| WO | WO-0134050 A2 | 5/2001 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009126575 A1 | 10/2009 |
| WO | WO-2009129477 A1 | 10/2009 |
| WO | WO-2010074986 A1 | 7/2010 |

OTHER PUBLICATIONS

"Local Lisa® Intracardiac Navigation System Model 9670000/9670025." Technical Manual Version 1.2, Chapter 1, pp. 1-19. 2004.
Brenner, David J., Ph.D., "Computed Tomography—An Increasing Source of Radiation Exposure", The New England Journal of Medicine (Nov. 29, 2007), pp. 2277-2284.
Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.
International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Preliminary Report on Patentability and Written Opinion for PCT/US2009/0400984 mailed Oct. 28, 2010, claiming benefit of U.S. Appl. No. 12/117,549, filed May 8, 2008.
International Preliminary Report on Patentability and Written Opinion for PCT/US2009/040979 mailed Oct. 28, 2010 claiming benefit of U.S. Appl. No. 12/117,537, filed May 8, 2008.
International Preliminary Report on Patentability and Written Opinion mailed Oct. 29, 2009 for PCT/US2007/089087, of which U.S. Appl. No. 12/492,906, filed Jun. 26, 2009 claims benefit.
International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.
International Search Report and Written Opinion for PCT/US2009/0400984 mailed Sep. 21, 2009, claiming benefit of U.S. Appl. No. 12/117,549, filed May 8, 2008.
International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Search Report and Written Opinion for PCT/US2009/067486 mailed May 4, 2010, claiming benefit of U.S. Appl. No. 12/336085, filed Dec. 16, 2008.
International Search Report and Written Opinion mailed Dec. 6, 2010 for PCT/US2010/051248, which claims benefit of U.S. Appl. No. 12/609,734, filed Oct. 30, 2009.
International Search Report and Written Opinon for PCT/US2009/040979 mailed Sep. 21, 2009 claiming benefit of U.S. Appl. No. 12/117,537, filed May 8, 2008.
International Search Report for PCT/US2007/089087 mailed Jul. 9, 2008, of which U.S. Appl. No. 12/492,906, filed Jun. 26, 2009 claims benefit.
Invitation to Pay Additional Fees for PCT/US2009/0400984 mailed Jul. 30, 2009, claiming benefit of U.S. Appl. No. 12/117,549, filed May 8, 2008.
Invitation to Pay Additional Fees for PCT/US2009/040979 mailed Jul. 30, 2009 claiming benefit of U.S. Appl. No. 12/117,537, filed May 8, 2008.
Invitation to Pay Additional Fees for PCT/US2009/067486 mailed Mar. 5, 2010, claiming benefit of U.S. Appl. No. 12/336,085, filed Dec. 16, 2008.
Invitation to Pay Additional Fees for PCT/US2010/047241 mailed Jan. 10, 2011, claiming benefit of U.S. Appl. No. 12/844,065, filed Jul. 27, 2010.
Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.
Markowitz, Toby, et al., "Unleaded: The Fluoroless 3D Lead Implant", Presented at Heart Rhythm Society, Denver, CO, (May 2007) 1 pg.
Markowitz, Toby, et al., Abstract Submission, "Unleaded: The Fluoroless 3D Lead Implant", Mar. 2007 2 pgs.
Milstein, S. et al., "Initial Clinical Results of Non-Fluoroscopic Pacemaker Lead Implantation." (pre-presentation abstract) May 14-17, 2008. 2 pgs.
Milstein, S. et al., "Initial Clinical Results of Non-Fluoroscopic Pacemaker Lead Implantation." (poster presentation) May 14-17, 2008. 1 pg.
Nelder, J.A., et al. "A simplex method for function minimization." vol. 7, Issue 4, (1965) pp. 308-313.The Computer Journal.
Savage, George, M.D., "Electric Tomography (ET)—A Novel Method for Assessing Myocardial Motion and Cardiac Performance", Heart Rhythm Society, Denver, CO (May 9-12, 2007) 1 pg.
Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.
Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.
Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.
Hubert-Tremblay, Vincent, et al. "Octree indexing of DICOM images for voxel number reduction and improvement of Monte Carolo simulation computing efficiency," Medical Physics, AIP , Melville, NY, US, vol. 33, No. 8, (Jul. 21, 2006) pp. 2819-2831, XP012092212, ISSN: 0094-2405, DOI: 10.1118/1.2214305 pp. 2820-2821.
International Preliminary Report on Patentability mailed Oct. 11, 2011 for PCT/US2010/030534 darning benefit of U.S. Appl. No. 12/421,375, filed Apr. 9, 2009.
International Search Report and Written Opinon mailed Jul. 25, 2011 for PCT/US2010/047241 claiming benefit of U.S. Appl. No. 12/844,065, filed Jul. 27, 2010.
International Search Report mailed Sep. 13, 2010 for PCT/US2010/030534 claming benefit of U.S. Appl. No. 12/421,375, filed Apr. 9, 2009.
Invitation to Pay Additional Fees mailed Jul. 7, 2010 for PCT/US2010/030534 claiming benefit of U.S. Appl. No. 12/421,375, filed Apr. 9, 2009.

* cited by examiner

CHRONICALLY-IMPLANTABLE ACTIVE FIXATION MEDICAL ELECTRICAL LEADS AND RELATED METHODS FOR NON-FLUOROSCOPIC IMPLANTATION

CROSS-REFERENCE TO RELATED APPLICATIONS

This application is a Continuation of International Application No. PCT/US2007/089087, filed Dec. 28, 2007. This application claims the benefit of U.S. Provisional Application No. 60/912,610, filed Apr. 18, 2007. The disclosures of the above applications are incorporated herein by reference.

STATEMENT OF INCORPORATION BY REFERENCE

This non-provisional U.S. patent application claims the benefit of the filing of the following provisional U.S. patent applications; namely: application Ser. Nos. 60/912,610; 60/882,420; 60/882,431; 60/882,435; 60/882,425; 60/882,428; 60/882,413 and each said application is hereby incorporated herein by reference in their respective entireties as if fully set forth herein.

FIELD OF THE INVENTION

The present invention relates generally to implantable medical devices (IMDs) and more particularly relates to electrical medical lead structures, systems and methods for collecting anatomical data of at least a portion of an anatomical organ or feature of interest using a non-fluoroscopically-based imaging system to thereby enable implantation of a chronically-implantable medical electrical lead (e.g., a cardiac pacing lead or the like).

BACKGROUND OF THE INVENTION

Prior art techniques relating to the instant invention include U.S. Pat. Nos. 5,983,126 and 5,697,377 to Wittkampf the contents of which are incorporated herein by reference. Wittkampf's work is based on orthogonal electric fields generated by the application of electrical energy to patches placed on the body. A system distributed by Medtronic, Inc., the LocaLisa® brand intra-corporeal navigation system, is at least partially based upon Wittkampf's work. In such a system, electrodes coupled to the skin of a subject provide orthogonal electrical fields (electrical potential-based fields) are used to locate the position of one or more electrodes coupled to an acutely implantable lead deployed within an organ or anatomical feature of interest. However, neither the system nor the acutely implantable lead provides the ability to precisely position and chronically implant a medical electrical lead, such as a cardiac pacing lead.

SUMMARY OF THE INVENTION

The present invention provides a rendering system termed herein an Implant sans Fluoro (IsF) system that essentially implements significant modifications to a Medtronic LocaLisa® navigation system to localize and track the position of electrodes on acutely implantable electrical leads (e.g., via transvenous pathways such as via the inferior or superior vena cava), such that a plurality of spaced-apart locations can be aggregated and rendered into a visual representation of an organ or anatomical feature of interest, among other features and capabilities.

Since a retractable helix-type lead is often preferred for chronic therapy delivery, and such a lead is difficult if not impossible to image using the IsF system, the inventors discovered that forming at least one aperture in a distal portion of the lead reveals enough metal of the helix (or other conductor) to fully image the location of the distal portion of the lead using the IsF system. As described, depicted and claimed herein, a sleeve-like member couples to the base of the retractable helix and thus seals the aperture(s) when the helix is deployed.

The IsF system utilizes the body's conductivity to determine electrode position. A Position Sensing Unit (PSU) introduces three small alternating currents (AC), each approximately 30 KHz into the body in three axes. Electrical currents are introduced through three pairs of patches applied to the patient's body surface. Electrodes on indwelling catheters are connected to the PSU. Signals from the three AC signal sources are resolved in the PSU and sent to a computer via serial I/O (SIO) communications channel. The IsF system monitors the SIO communications and processes position data from the PSU to provide a position display. The PSU has a foot pedal for the implanting physician. When the foot pedal is depressed, IsF prompts the physician with a list of labels to landmark the present location of the catheter electrodes. A joystick for the physician is used to select labels for foot pedal marked landmarks. The IsF system is designed to be used with indwelling electrodes on catheters and can be designed to visualize locations via leads having one or multiple electrodes. The IsF system can utilize a reference electrode placed at the xiphoid process (also known as the cardiac notch) allows IsF to display the patient midline which provides additional visual cues to a user during collection of electrode data.

In one form of the present invention, for example, a modified Medtronic model 5076 or a model 3830 endocardial pacing lead can be chronically implanted following collection of data of the electrode locations. For example, a model 5076 lead can be deployed into a desired cardiac chamber (e.g., via a Medtronic SelectSite™ model 6226DEF deflectable sheath catheter for a ventricular chamber and a model C304-S59 for the right atrial chamber). An Edwards Lifesciences brand Swan-Ganz Bipolar Pacing Catheter (REF: D97120F5) can be used for exploration leading to placement of the ventricular pacing lead. Note that the Edwards balloon catheter is 5F outer diameter, thus requiring the model of deflectable sheath listed above. The balloon catheter has two electrodes, one distal and one proximal to the balloon used for presenting electrograms. Of course, according to the invention other suitable combinations of modified active fixation-type pacing or defibrillation cardiac pacing leads, introducer instruments, and exploration catheters can be used per the present invention.

A pacemaker or ICD (e.g., a single, dual or triple chamber device) optionally having CRT delivery capability can utilize electrode configured per the present invention. If a single chamber ventricular pacemaker is to be implanted, the steps for implantation of the atrial are omitted. If a single chamber atrial pacemaker is to be implanted, exploration steps using the balloon catheter for the ventricular lead will be followed to provide three dimensional landmarks. Once obtained and the balloon deflated, a ventricular lead will not be introduced. The procedure will then progress to introduction of the atrial lead.

A Medtronic brand implantable pulse generator (pacemaker) including chamber capture management can be used to track pacing thresholds on an ambulatory basis post implant to make the chronically lead remains fixed to the desired locations. Such pacemakers include without limitation the EnPulse, Adapta, Versa, and Sensia brand IMDs. Display of physiological data shall be with instrumentation provided by the investigating center. These data can include the electrocardiogram (ECG), electrograms (EGM) from indwelling catheter electrodes, and pressure of an inflated balloon disposed on a distal portion of an electrode-bearing elongated structure.

DESCRIPTION OF THE DRAWINGS

The present invention will hereinafter be described in conjunction with the following drawing figures, wherein like numerals denote like elements.

DETAILED DESCRIPTION OF ILLUSTRATED EMBODIMENTS

Figure 1:
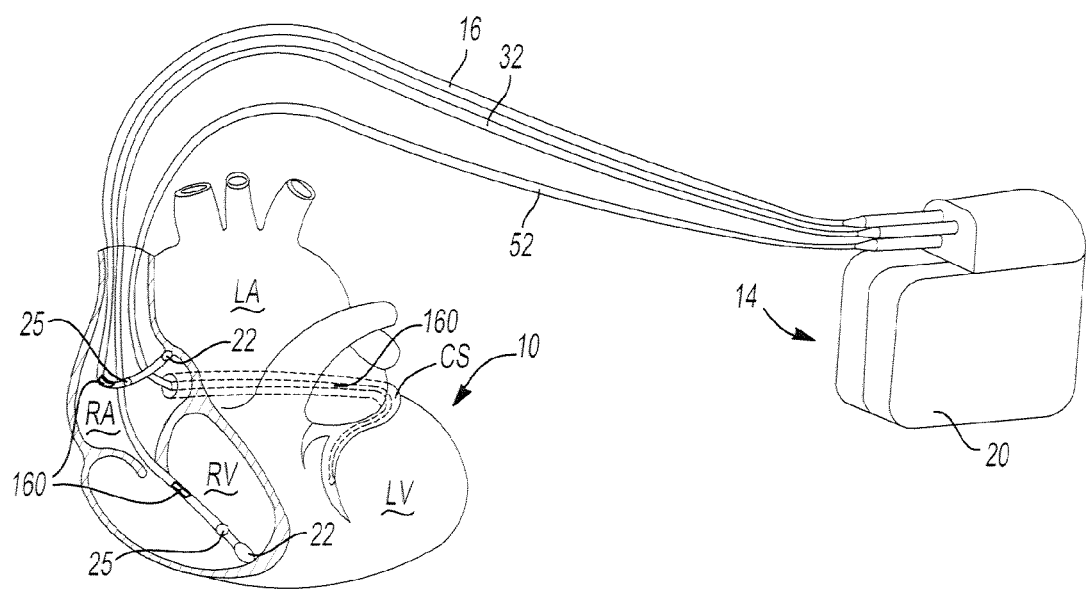
FIG. 1 is a schematic diagram depicting a multi-channel, atrial and bi-ventricular, monitoring/pacing implantable medical device (IMD) in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Certain embodiments of the invention may provide a noninvasive technique for monitoring the position, movement, and/or geometric characteristics of internal body tissue, such as cardiac muscle tissue. For example, such information may enhance the ability to assess certain parameters (e.g., parameters related to cardiac performance), and may also affect therapy delivery decisions. In one particular embodiment, for example, measuring the position and movement of leads appropriately placed in the heart for long-term therapy delivery.

Position and motion information for a given body tissue may be monitored by measuring a voltage signal induced in an electrode coupled to the body tissue of interest, the electrode being adapted to move in conjunction with movement of the body tissue. One or more electric fields may be applied through the tissue of interest to cause the voltage to be induced in the electrode, according to certain embodiments of the invention. Certain embodiments of the invention may include, or may be adapted for use in, diagnostic monitoring equipment, external medical device systems, and implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

An embodiment of the invention includes a system for monitoring movement of internal body tissue, such as cardiac muscle tissue. The system may include one or more pairs of surface electrodes disposed about the body tissue capable of supplying an electric field through the body tissue between the surface electrodes. The position and movement of the body tissue may be detected by coupling an internal electrode to the body tissue, and measuring a voltage induced therein, the induced voltage being a function of the position between the two surface electrodes. The voltage induced on the internal electrode may be provided to the system as a position signal for monitoring and/or recording.

In certain embodiments, position signals corresponding to the movement of one or more internal electrodes may be used to determine measures of cardiac performance, including systolic and diastolic cardiac function. In certain embodiments, a second and third pair of surface electrodes may be used to generate position information signals with respect to three axes of geometry to thereby provide a three-dimensional position signal.

In certain embodiments of the invention, the system may be used in conjunction with an implantable cardiac rhythm management/monitoring device. An implantable medical device (IMD) may be coupled to standard implantable leads (e.g., cardiac pacing leads), which may serve as the internal electrodes of the system for monitoring movement of body tissue. In such an embodiment, movement of body tissue (e.g., cardiac muscle tissue) may cause corresponding movement of the implantable leads. The implantable leads, when exposed to the electric field signals, may have a voltage induced, which may be sensed by the IMD and either stored in memory, processed, or telemetered out to a programmer for further processing. In some embodiments, the IMD may process location information and/or determine measures of cardiac performance, and may store such information for later retrieval. In some embodiments, the telemetered voltage signals may be processed by a programming system or computer to generate position information, as well as to compute various measures of cardiac performance, such as left ventricular dimension, for example.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM). In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
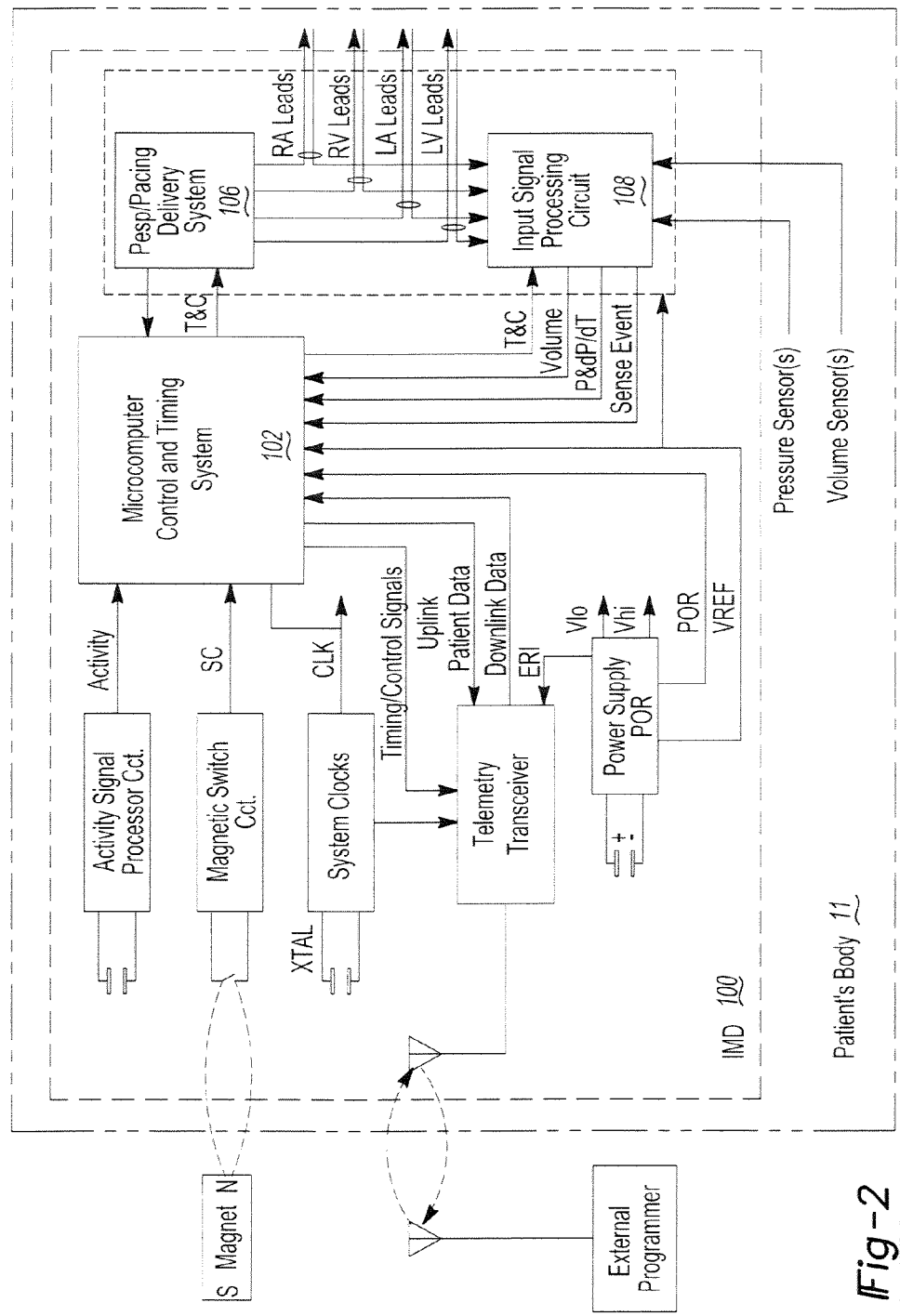
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors.

Figure 3:
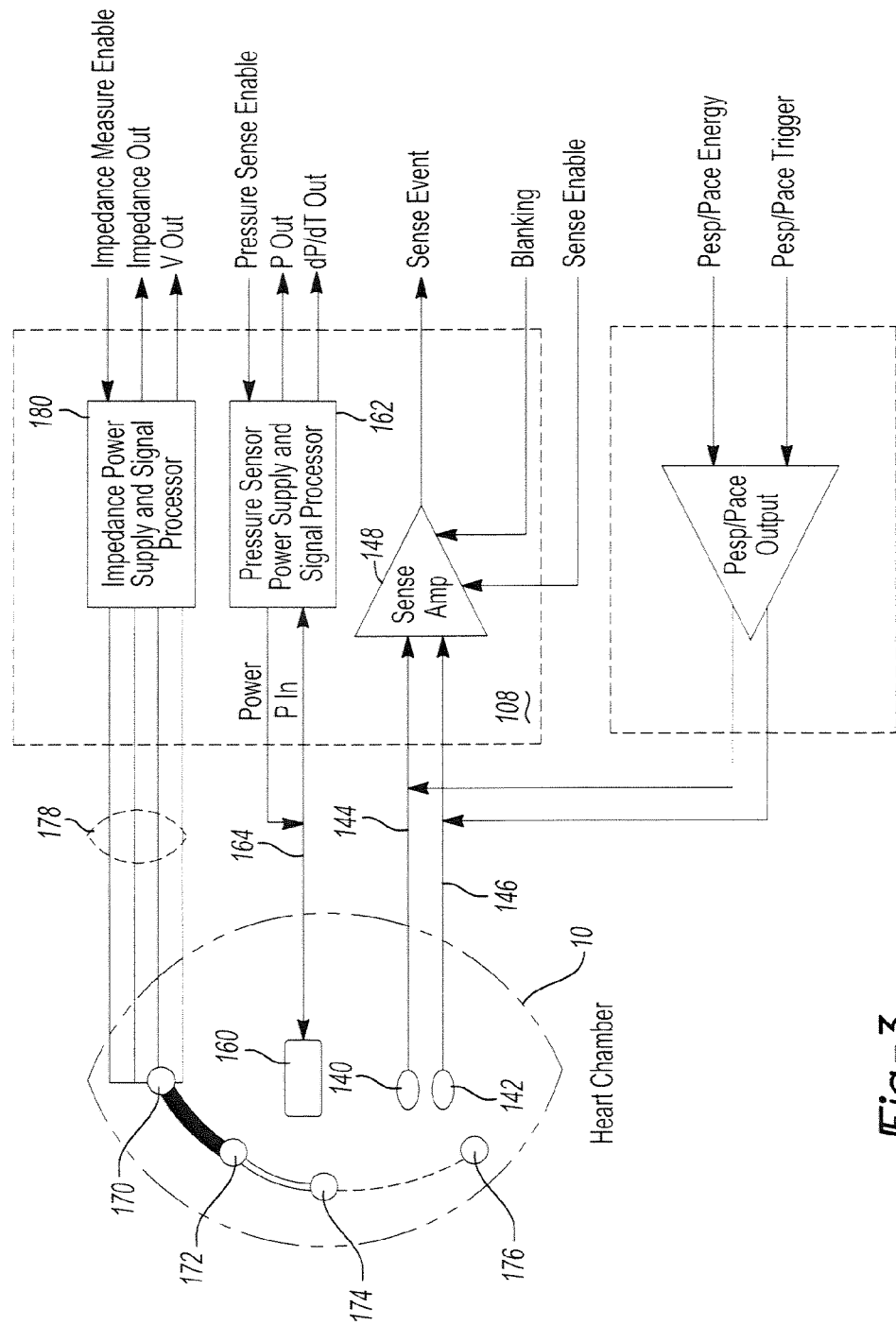
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

Figure 4:
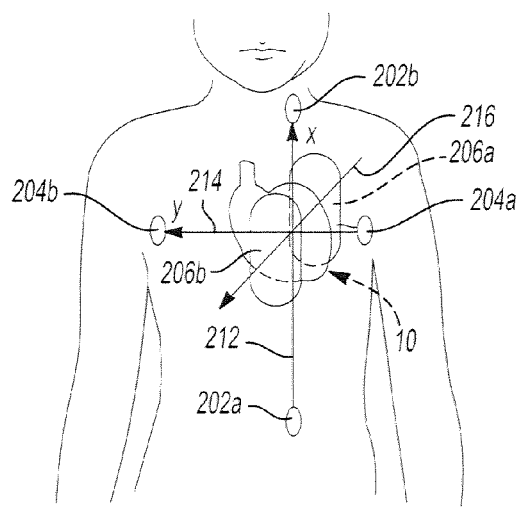
FIG. 4 is a schematic illustration of a plurality of surface electrodes generating electric fields that pass through a body tissue of interest, according to an embodiment of the invention.

FIG. 4 shows a schematic illustration of a plurality of surface electrodes (e.g., electrode patches) applied to a patient's skin to generate electric fields that pass through body tissue of interest, such as heart 10, according to certain embodiments of the invention. The electric fields may be generated by applying a voltage across a pair of generally planar surface electrodes (e.g., patch electrodes 202a, 202b, 204a, 204b, 206a, and 206b), which may be applied externally to a patient's skin, or may be implanted subcutaneously according to certain embodiments. In some embodiments, the voltage for generating the electric fields may be supplied by a small device worn by a patient, for example, and applied to the planar electrodes.

One or more electrodes may be coupled to a body tissue of interest, for example at a number of locations in a patient's heart muscle. Movement of the body tissue (e.g., the heart muscle) may be roughly equivalent to movement of the electrodes coupled to the body tissue of interest. By monitoring the movement of the electrodes over time, it may be possible to monitor movement, and thus geometric characteristics of the body tissue of interest. Obtaining position information on the one or more electrodes may be accomplished by sensing a voltage induced on the electrode from the presence of an electric field directed towards the body tissue of interest.

As shown in FIG. 4, patch electrodes 202a and 202b may be positioned to generate an electric field that travels between electrodes 202a and 202b, defining an axis 212. Thus, the position of an electrode along axis 212 (and hence, movement with respect to axis 212) may be determined by measuring a voltage induced on the electrode as a function of time. An electrode (or electrodes) coupled to the heart 10 (or portions thereof) may therefore provide position and movement information with respect to axis 212. Similarly, electrodes 204a and 204b may provide an electric field through the heart 10 along axis 214, and electrodes 206a and 206b may provide an electric field through the heart along axis 216. As shown, axes 212, 214, and 216 may be orthogonal axes to describe three-dimensional position information. In certain embodiments, one or two axes may be employed to describe one- and two-dimensional position information, respectively.

Figure 5:
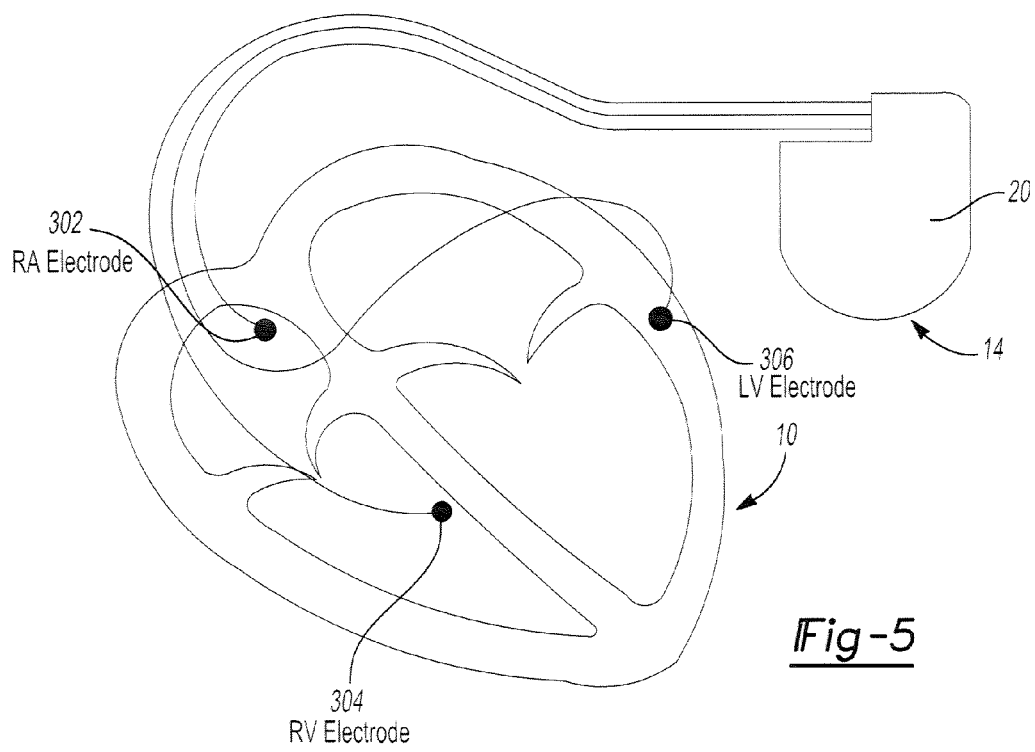
FIG. 5 is a schematic illustration of an internal electrode system that may be used to monitor cardiac tissue, according to an embodiment of the invention.

FIG. 5 shows an exemplary 3-lead system, having electrode locations in the right ventricle, the right atrium and in the left ventricle (e.g., via the coronary venous circulation) of a patient's heart 10. In general, the lead electrodes can be positioned such that they span a particular dimension of interest, which may provide monitoring of heart chamber characteristics throughout the cardiac cycle, according to certain embodiments.

Voltage measurements may be taken relative to a stable reference electrode, such as the can electrode of IMD 14, or a stable reference electrode on a lead located within the heart 10, for example. At any given time, each lead electrode will have associated x, y, and z position coordinates. By applying electric fields to orthogonal pairs of surface electrodes placed on the patient, each implanted electrode will produce sensed voltages ($V_x$, $V_y$, $V_z$) that reflect the voltage difference between the lead electrode and the reference as a function of lead electrode position along each orthogonal axis. Assuming homogeneous body conductance, each voltage will be linearly related to the lead electrode position in each orthogonal axis. The location of the implanted electrodes in each of the 3 axes can thereby be determined.

To reduce the effect of varying skin contact impedance, the electric field(s) may be established through the use of constant current sources. In embodiments having more than one axis, the electric fields along each axis may be distinguished from each other by employing a unique characteristic of the constant current source, such as frequency, phase or time. This identifying characteristic allows the induced voltages corresponding to each axis to be distinguished and processed separately. The effect of patient respiration on the sensed voltages may be filtered out using a suitable bandpass filter in certain embodiments of the invention.

A simple calibration scheme could use the bipolar electrode configuration with known interelectrode distance on any of the leads. Standard IPG bipolar leads can be used for that purpose. Calibration can be performed automatically on a regular basis to account for changing tissue sensitivities and changes in lead orientation.

In another deployment scheme, two or more electrodes could be deployed on the outer surface of the myocardium and then connected to the IPG.

Figure 6A:
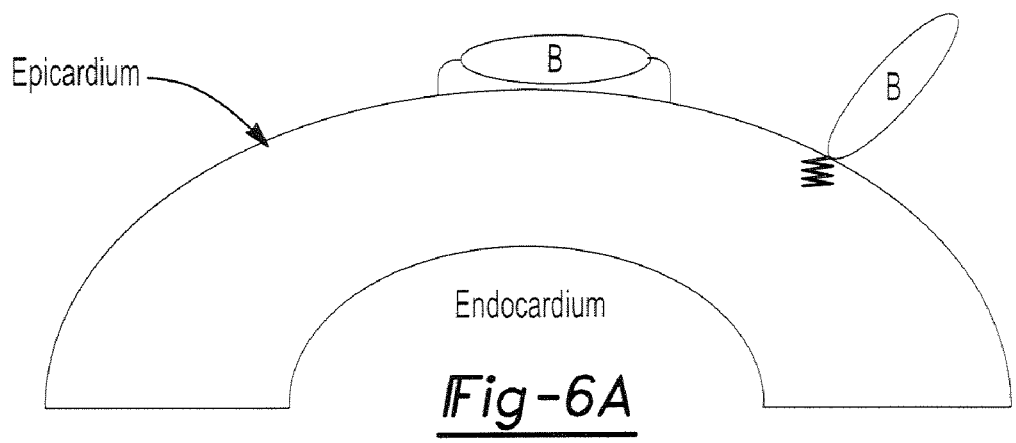
FIGS. 6(*a*)-(*c*) show cross-sectional views of endocardial and epicardial electrode locations for monitoring cardiac tissue in accordance with certain embodiments of the invention.
Figure 6B:
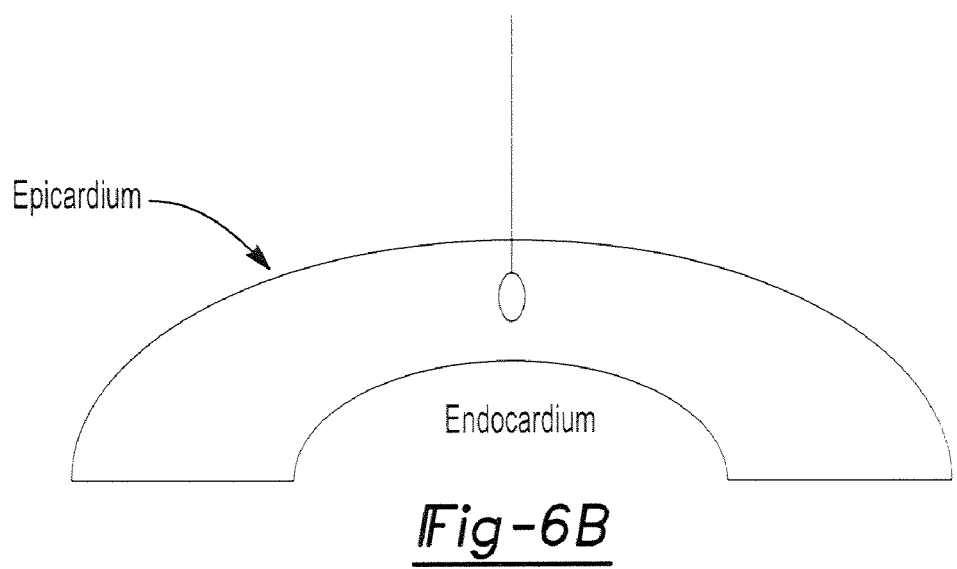
Figure 6C:
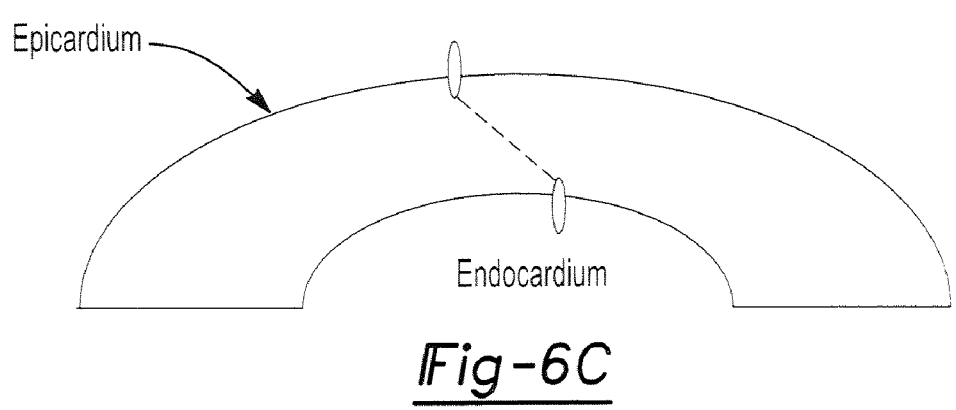

FIGS. 6(*a*)-(*c*) show cross-sectional views of endocardial and epicardial electrode locations for monitoring cardiac tissue in accordance with certain embodiments of the invention.

Some electrode locations may be positioned close to the patch electrodes on the skin. If the skin patches are not sufficiently large, the electric field lines may be slightly curved leading to a minor error in the measurement. In the preferred embodiment, the skin electrodes in the z-direction in FIG. 1 are larger than the skin electrodes in the other 2 directions to account for the proximity of the z-electrodes to the heart.

Techniques to generate a voltage measurement on an IPG lead from externally applied orthogonal fields: In one embodiment, the applied fields are frequency division multiplexed such that each axis is excited by a different frequency. In another embodiment, the fields are generated using time-division multiplexing such that each axis is excited by the same frequency signal at a predetermined time. The magnitude of the sensed voltage from each of the applied axis fields would vary in proportion to the lead position relative to the applied field. In one embodiment employing frequency division multiplexing, a narrowband filter is centered at the frequency corresponding to each axis. The output of each of the three narrowband filters is processed to show a time trace of the magnitude or energy in the corresponding band. At any time instant the three generated traces would indicate the magnitude of the voltage senses in each axis. Position information can then be calculated using the calibration parameters and a stationary electrode that provides a common reference for all voltage senses.

Figure 7:
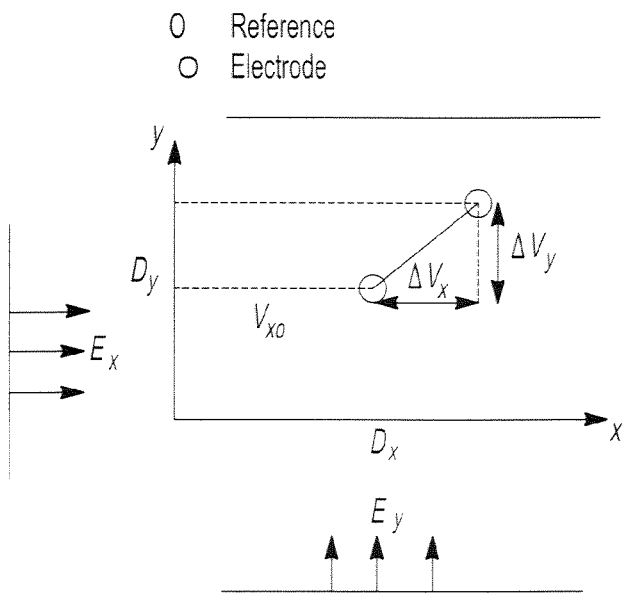
FIG. 7 is a two-dimensional plot illustrating the calculation of position information according to an embodiment of the invention.
Figures 8A, 8B, 8C, 8D:
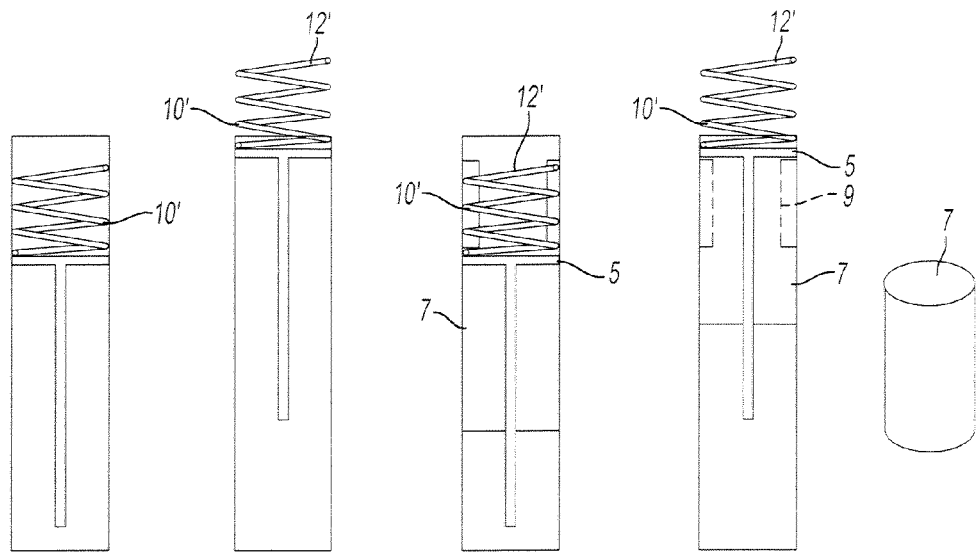
FIG. 8A-D is an elevational view schematically depicting a prior art (Medtronic model 5076) retractable helix lead and an embodiment according to the present invention.

FIG. 7 is a two-dimensional plot illustrating the calculation of position information according to an embodiment of the invention. Techniques to generate electric fields from a small wearable device capable of delivering frequencies in the range 5-50 kHz on three essentially orthogonal axes: The device should be battery operated and be capable of extended use if used in an ambulatory setup. Calibration techniques to convert voltage measurements to position information: In one embodiment, at least one lead will have a bipolar configuration (tip-ring) with known inter-electrode distance. By placing the electrodes in the electric field, each electrode will sense voltages from the three axes. The magnitude of the voltage sense in each direction is proportional to the distance from one of the patches generating the field in that direction. The constant of proportionality is related to the medium and the field strength. In one embodiment, the three orthogonal fields are identical and the calibration step can be done with a single measurement. In this system, the implanted device has no information regarding the current for each of the electrodes unless it is coded into the external generator and so transmitted to the implanted device. If the external generator regulates the applied voltage to each of the three pair of patch electrodes, such that current through each of the three is equal, then a corresponding movement by each electrode will generate the same voltage change for equivalent position change in each axis. In this manner, one millimeter of movement in any of the x, y, or z directions will produce the same magnitude voltage change.

FIGS. 8A-D are elevational views schematically depicting a prior art (Medtronic model 5076) retractable helix lead and an embodiment according to the present invention. At least one aperture, or window, 9 is formed in a lateral portion of the proximal end portion of the lead adjacent to a part of the helix 10 (when retracted). A corresponding cover structure (e.g., a sleeve member) 7 couples to a base portion 5 of the helix 10' such that when the helix 10' is retracted the metallic or conductive helix 10' can be imaged using electropotential (or electromagnetic) fields such as via a derivative of a LocaLisa® brand non-fluoroscopic imaging system. The sleeve 7 effectively seals and covers the aperture(s) 9 when the helix 10' is deployed following implantation and thus avoids possible contamination or ingress of body fluids over the long term.

Figure 9:
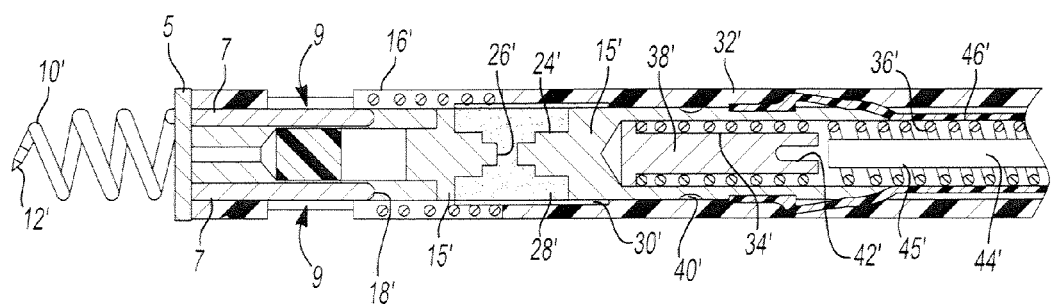
FIG. 9 is an elevational side view in cross section of an embodiment of an active fixation lead according to the invention.

FIG. 9 is a side, cut away view through the distal end of pacing lead according to the present invention. At the very distal end of the lead, a sharpened helix 10 is located, which extends distal to the distal portion of the lead body. Helix 10 is preferably conducted of an inert, biocompatible metal such as MP35N alloy, Elgiloy alloy, or a platinum alloy. As illustrated, helix 10' is generally a conical, tapered helix and the sharpened, distal end 12' of the helix is located intersecting the central axis of the lead. The lead is provided with an electrode head member 14', to which helix 10' is mounted by means of a plastic sleeve 16' in which the proximal end of helix 10' is embedded. Sleeve 16' may be fabricated of polyurethane or silicone rubber. Thus, at least one aperture, or window, 9 is formed in a lateral portion of the proximal end portion of the lead adjacent to a part of the helix 10 (when retracted). A corresponding cover structure 7 couples to a base portion 5 of the helix 10' as previously described.

Located within head member 14' is an electrode chamber 18' which contains a monolithic controlled release device impregnated with a glucocorticosteroid, delivered to the distal end of the electrode head member 14' by means of a longitudinal bore 22', which may be filled with a porous, sintered structure to control elution rate of the steroid. Details of construction related to such electrodes are found in U.S.

Pat. No. 4,506,680, issued to Stokes, incorporated herein by reference in its entirety. For the purpose of the present invention, it is only important that an electrode of some sort be included in the pacing lead. In some cases, the helix 10 may serve as the electrode.

Electrode head member 15' forms the proximal portion of the electrode head assembly and is provided with a circumferential groove 24', and with a cross bore 26'. Groove 24' and cross core 26' are preferably filled with an implantable medical plastic 28' which may be either silicone rubber or polyurethane. A circular band of adhesive 30 surrounds plastic 28, and serves to seal the proximal end of plastic sleeve 16' and the distal end of an insulative sleeve 32' to the electrode head member 14'.

Located within the proximal end of electrode head member 14' is a second bore 34', which receives the distal end of the coiled conductor 36'. Coiled conductor 36' is electrically and mechanically coupled to electrode head member 14' by means of a crimping core 38', in conjunction with inwardly directed crimps 40' in head member 14'. This mechanical connection mounts the conductor in fixed rotational relationship to the helix 10', allowing for transfer of torque to helix 10' via conductor 36'. The distal end of crimping core 38' is provided with a slot 42' located at its proximal end, which engages the distal end of a screwdriver tipped stylet 44' in fixed rotational relationship. An elongated insulative sheath 46' is mounted between insulative sleeve 32' and head member 14', and extends proximally to the proximal end of the lead. Sheath 46' is preferably made of an implantable elastoplastic such as silicone rubber or polyurethane. In bipolar embodiments, a second, ring electrode may be located on the lead body, coupled to a second coiled conductor. These optional structures are not illustrated.

In use, the distal end of the lead illustrated in FIG. 9 is advanced through the venous system, the superior vena cava and through the tricuspid valve and rotated so that helix 10' pierces the endocardium and is screwed into the interior wall of the heart. While screwing helix 10' into the heart tissue, it is desirable that stylet 44' be engaged with the slot 42' in crimping core 38' and that the stylet and the lead body be rotated simultaneously, so that both structures work together to apply torque to the electrode head member 14' and thus to the helix 10'.

While the present invention is disclosed in the context of a pacing lead employing a fixed helix, it is believed that it may also be employed in the context of any lead employing an advanceable or rotatable helix of the type in which the fixation helix is rotationally fixed with regard to the distal end of the coiled conductor within the lead body. As such, the above embodiments should be considered exemplary, rather than limiting, in conjunction with the following claims.

Thus, various methods and apparatus have been provided so that those skilled in the art can practice same. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A medical electrical lead, comprising:
   an elongated medical lead body having a proximal end and a distal end;
   at least one elongated electrical conductor disposed within the lead body;
   an aperture formed through a distal portion of said lead body, wherein said aperture is spaced from the distal end of said lead body and whereby the aperture exposes a portion of the elongated conductor, wherein a retractable and extendable portion of the elongated conductor is disposed adjacent the aperture and the portion comprises a non-linear portion; and
   a substantially flat structure coupled to the non-linear portion, and wherein the flat structure is slideably disposed within the lead body.

2. A medical electrical lead, comprising:
   an elongated medical lead body having a proximal end and a distal end;
   at least one elongated electrical conductor disposed within the lead body;
   an aperture formed through a distal portion of said lead body, wherein said aperture is spaced from the distal end of said lead body and whereby the aperture exposes a portion of the elongated conductor, wherein a retractable and extendable portion of the elongated conductor is disposed adjacent the aperture; and
   a sealing member coupled to the at least one elongated electrical conductor so that when the portion is extended the sealing member substantially seals the aperture.

3. A lead according to claim 2, further comprising means for manipulating the retractable and extendable portion coupled to a portion of the proximal end of the lead body.

4. A lead according to claim 2, wherein the lead body comprises a temporary cardiac pacing lead.

5. A medical electrical lead, comprising:
   an elongated medical lead body that comprises a cardiac pacing lead having a proximal end and a distal end;
   at least one elongated electrical conductor disposed within the lead body;
   an aperture formed through a distal portion of said lead body, wherein said aperture is spaced from the distal end of said lead body and whereby the aperture exposes a portion of the elongated conductor;
   a sealing member moveable to seal the aperture;
   an elongated high voltage conductor disposed within the lead body; and
   a length of coiled conductor coupled to the high voltage conductor, wherein the coiled conductor is disposed around the periphery of the lead body.

6. A medical electrical lead, comprising:
   an elongated medical lead body having a proximal end and a distal end;
   at least one elongated electrical conductor disposed within the lead body;
   an aperture formed through a distal portion of said lead body, wherein said aperture is spaced from the distal end of said lead body and whereby the aperture exposes a portion of the elongated conductor;
   a plurality of apertures formed in a portion of the lead body, wherein each of the plurality of apertures exposes a portion of the elongated conductor; and
   a like plurality of sealing members, said sealing members adapted to simultaneously seal the plurality of apertures when manipulated from a portion of the proximal end of said lead body.

7. A medical electrode lead, comprising:
an elongated lead body including an elongated coiled conductor mounted within an elongated insulative sheath;
an electrode head mounted to a distal end portion of said coiled conductor, and including a helical means for fixation of the electrode head adjacent body tissue to be stimulated, said helical fixation means mounted in a fixed rotational relationship to said coiled conductor;
a connector means mounted at a proximal end of said coiled conductor for coupling to said coiled conductor, mounted in fixed rotational relationship to said coiled conductor;
a stylet insertable within said coiled conductor;
means for mounting said stylet in fixed rotational relationship to both said connector means and said helical fixation means, wherein at least one aperture is disposed proximate said helical means for fixation, said at least one aperture spaced from the distal end of medical electrode lead; and
means for sealing said at least one aperture.

8. A lead according to claim 7 wherein said elongated coiled conductor is mounted in fixed rotational relationship with said electrode head and with said elongated insulative sheath.

9. A lead according to claim 8 further comprising: means for transferring torque from the proximal end of said elongated insulative sheath to said helix.

10. A lead according to claim 9 further comprising a stylet insertable within said elongated insulative sheath; means for mounting said stylet in fixed rotational relationship to both said helix and said proximal end of said elongated insulative sheath.

11. A medical electrode lead comprising:
an elongated insulative sheath having a proximal and distal end and defining an aperture through the sheath;
an elongated conductor having a proximal end and a distal end and mounted within said elongated insulative sheath;
an electrode head mounted to the distal end of said conductor, and including a helical means for fixation of said electrode head adjacent body tissue to be stimulated, said helical fixation means mounted in fixed rotational relationship to said electrode head;
a connector assembly mounted to the proximal end of said elongated insulative sheath, and including an electrical connector coupled to the proximal end of said elongated conductor;
a stylet insertable within said elongated insulative sheath; and
a sealing member moveable with the electrode head to seal the aperture.

12. A lead according to claim 11, wherein said conductor comprises a coiled conductor and wherein said fixation means is mounted in fixed rotational relationship to said coiled conductor and wherein said connector assembly is mounted in fixed rotational relationship to said coiled conductor.

* * * * *